US005474776A

United States Patent [19]
Koyanagi et al.

[11] Patent Number: 5,474,776
[45] Date of Patent: Dec. 12, 1995

[54] COSMETIC COMPOSITION

[75] Inventors: Hidenobu Koyanagi, Yono; Takeshi Morita, Tokyo; Akiko Suzuki, Chiba; Akira Shigeta, Hasaki, all of Japan

[73] Assignee: Kao Corporation, Tokyo, Japan

[21] Appl. No.: 86,038

[22] Filed: Jul. 6, 1993

[30] Foreign Application Priority Data

Jul. 3, 1992 [JP] Japan .................................. 4-177015

[51] Int. Cl.⁶ .............................. A61K 7/02; A61K 7/48
[52] U.S. Cl. ...................... 424/401; 424/78.02; 514/844; 514/846; 514/944
[58] Field of Search .................. 424/401, 78.02, 424/195.1; 514/844, 845, 846, 847, 944; 252/299.01, 122, 132, 162, 173, 174.11, 174.17, 174.22, 174.23, 311, 312, 315.01, 315.1, 315.3, 315.4, 351, 356

[56] References Cited

U.S. PATENT DOCUMENTS 4,767,625  8/1988  Mitsuno et al. ........................ 424/95
5,015,471  5/1991  Birtwistle et al. ...................... 424/70

Primary Examiner—Jyothsna Venkat
Attorney, Agent, or Firm—Oblon, Spivak, McClelland, Maier & Neustadt

[57] ABSTRACT

A transparent or translucent cleansing composition in the form of gel or liquid includes (A) a hydrophilic nonionic surfactant, (B) an amphoteric surfactant, (C) a water-soluble compound containing at least one hydroxyl group, (D) a liquid oil and (E) water. The cleansing composition provides an agreeable feeling during use, is excellent in spreadability and slidability upon application to the skin, and is good in penetrability into minute parts of the skin. It also avoids ready increase in viscosity even when additional water is mixed therein, can be used in massaging the skin while keeping it smooth to the touch during its application, is suitable for use even in wet environments, such as a bathroom, and can be removed with ease from the skin using only water, so that the base component does not remain on the skin. The composition is excellent in detergency and rinsability and gives users a refreshed feeling after use. The composition is also stable during long term storage, even at elevated temperatures.

2 Claims, No Drawings

COSMETIC COMPOSITION

BACKGROUND OF THE INVENTION

1. Field of the Invention

The present invention relates to a cosmetic composition, and more specifically to a transparent or translucent cosmetic composition in the form of a gel or liquid, which spreads well, has good penetrability into minute parts of the skin, avoids an increase in viscosity even when additional water is mixed therein, gives users a pleasant feeling during use and is useful as a cleansing or massaging cream.

2. Description of the Background Art

There are a variety of cosmetic preparations, such as cleansing cosmetic preparations and massaging cosmetic preparations, which are used to remove dirt or makeup preparations by applying an oil component to the skin, spreading the oil on the skin, and removing the oil and dirt or makeup from the skin after the desired cleansing effect has been achieved. Such cosmetic preparations include those of an oil form, a cream of an oil-in-water type or water-in-oil type emulsion, or a gel of an oil-in-surfactant type emulsion. Many of these are commercially available.

However, these conventional cleansing and massaging cosmetic preparations containing an oil component have as a distinct disadvantage that they are sticky to the touch upon use and poor in storage stability.

In recent years, cleansing cosmetic preparations and massaging cosmetic preparations which have a liquid crystal structure due to the presence of a hydrophilic nonionic surfactant have been reported as one technique for curing this disadvantage (Japanese Patent Publication No. 53845/1989, corresponding to Mitsuno et al, U.S. Pat. No. 4,767,625).

However, these preparations containing liquid crystal structures are disfavored because they are unfit for use while sweating or under wet conditions such as in a bathroom. The viscosity of these compositions tends to increase to unacceptable levels due to the mixing of water therein, causing poor spreading characteristics.

There has thus been a demand for development of a composition which spreads well upon application to the skin, is easy to use in massaging, is free from unacceptable increases in viscosity even when water is mixed therein, can be completely removed with water alone without the necessity of wiping the composition off prior to removal by water, is excellent in cleansing quality, is not sticky to the touch upon use, gives users a pleasant feeling upon use and can be used as a cleansing or massaging cosmetic preparation.

SUMMARY OF THE INVENTION

Accordingly, one object of the present invention is to provide a composition which overcomes the above-described problems.

A further object of the present invention is to provide a composition which spreads well upon application to the skin, is easy to use in massaging, can be completely removed with water alone without the need to wipe the composition off prior to removal with the water, provides excellent cleansing properties, provides a pleasant feeling upon use.

A further object of the present invention is to provide a composition with the above advantages which can be used as a cleansing or massaging cosmetic preparation.

Another object of the present invention is to provide a composition having the above advantages which is stable during long term storage even at elevated temperatures.

These and other objects which will become readily apparent upon reading the following detailed description have been satisfied by the discovery of a composition comprising:

(A) a hydrophilic nonionic surfactant;
(B) an amphoteric surfactant;
(C) a water-soluble compound containing at least one hydroxyl group;
(D) a liquid oil; and
(E) water.

In another aspect of the present invention, there is also provided a composition which comprises, in addition to the above components (A) to (E), as an additional component (F): an addition compound of a sugar derivative and ethylene oxide or propylene oxide.

DETAILED DESCRIPTION OF THE PREFERRED EMBODIMENTS

The present invention relates to cosmetic compositions comprising:

(A) a hydrophilic nonionic surfactant;
(B) an amphoteric surfactant;
(C) a water soluble compound having at least one hydroxyl group;
(d) a liquid oil; and
(e) water.

Optionally, component (F), an addition compound of a sugar derivative and ethylene oxide or propylene oxide, may be added.

The cosmetic compositions according to the present invention are in the form of gel or liquid, which is easy to handle, gives users an agreeable feeling upon use, i.e., is excellent in spreadability and slidability upon application to the skin, and are good in penetrability into minute parts of the skin.

The compositions of the present invention may be transparent or translucent.

The compositions do not exhibit a ready increase in viscosity even when water is added from the outside, can be used in massaging the skin while keeping them smooth to the touch during their application, and are suitable for use even in wet environments, such as in a bathroom. In addition, when water is added to the composition of the present invention, the oil component in the composition forms extremely fine water-emulsified particles of oil which can be removed with ease from the skin, together with dirt such as makeup. Thus, the base component does not remain on the skin, excellent detergency and rinsability and giving users a refreshed feeling after use.

While any hydrophilic nonionic surfactant may be used as component (A) of the present invention, those having an HLB higher than 9 are preferred.

As used in the present invention, the term "HLB" denotes hydrophilic-lipophilic balance, as calculated in accordance with the following equation by Oda, Teramura et al.

$$HLB = \frac{\Sigma \text{ inorganic value}}{\Sigma \text{ organic value}} \times 10$$

Examples of the hydrophilic nonionic surfactant having an HLB greater than 9 include polyoxyalkylene type nonionic surfactants such as polyoxyethylene alkyl ethers, polyoxypropylene alkyl ethers, polyoxyethylene alkylphenyl ethers, polyethylene glycol fatty acid esters, ethylene oxide derivatives of propylene glycol fatty acid esters, polyoxyethylene sorbitan fatty acid esters, ethylene oxide derivatives of mono- or polyglycerol fatty acid esters, ethylene oxide derivatives of trimethylolpropane fatty acid esters, polyoxyethylene hardened castor oils, polyoxyethylene hardened castor oil fatty acid esters, polyoxyethylene hardened castor oil pyroglutamate and polyoxyethylene glycerol pyroglutamate; sucrose fatty acid esters; alkylglucosides; polyglycerol fatty acid esters; and polyglycerol alkyl ethers. The hydrophobic groups of these nonionic surfactants, such as alkyl and phenyl groups and fatty acid residues, preferably have 8–36 carbon atoms. Specific examples thereof include polyoxyethylene (30) hardened castor oil, polyoxyethylene (40) hardened castor oil, polyoxyethylene (50) hardened castor oil, polyoxyethylene (60) hardened castor oil, polyoxyethylene (15) decyltetradecyl ether, polyoxyethylene (20) decyltetradecyl ether, polyoxyethylene (25) decyltetradecyl ether, polyoxyethylene (10) hexyldecyl ether, polyoxyethylene (15) hexyldecyl ether, polyoxyethylene (20) hexyldecyl ether, polyoxyethylene (25) hexyldecyl ether, polyoxyethylene (10) octyldodecyl ether, polyoxyethylene (16) octyldodecyl ether, polyoxyethylene (20) octyldodecyl ether, polyoxyethylene (25) octyldodecyl ether, polyoxyethylene (15) glycerol monoisostearate, polyoxyethylene (30) glycerol monoisostearate, polyoxyethylene (30) glycerol triisostearate, polyoxyethylene (40) glycerol triisostearate, polyoxyethylene (30) trimethylolpropane trimyristate, polyoxyethylene (6) sorbitan monolaurate, polyoxyethylene (20) sorbitan monolaurate, polyoxyethylene (20) sorbitan monostearate, polyoxyethylene (20) sorbitan monooleate, polyoxyethylene (30) sorbitol tetraoleate and polyoxyethylene (40) sorbitol tetraoleate. Of these, the polyoxyethylene alkyl ethers, polyoxyethylene sorbitan fatty acid esters and polyoxyethylene hardened castor oils are particularly preferred.

The compounds of component (A) may be used either singly or in any combination thereof, and are preferably incorporated in a range of 1–30 wt. % (hereinafter indicated merely by %), more preferably 5–25%, based on the total composition of the cosmetic composition according to the present invention. Proportions lower than 1% may result in a cosmetic composition having insufficient detergency and rinsability, while proportions exceeding 30% may result in a cosmetic composition which undergoes viscosity increase or solidification.

Suitable examples of the amphoteric surfactant of the component (B) useful in the composition of the present invention, include amine oxides represented by the following general formula (1):

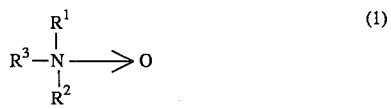

wherein $R^1$ and $R^2$ are each, independently an alkyl, alkoxy or hydroxyalkyl group having 1–4 carbon atoms, and $R^3$ denotes an organic group having 8 or more carbon atoms, such as straight chain or branched alkyl having from 8 to 30 carbon atoms, preferably 8 to 24 carbon atoms, or straight chain or branched alkenyl having from 8 to 30 carbon atoms, preferably 8 to 24 carbon atoms.

Preferred examples of such amine oxides, include lauryldimethylamine oxide, myristyldimethylamine oxide, cetyldimethylamine oxide, stearyldimethylamine oxide, oleyldimethylamine oxide, heptadecyldimethylamine oxide, behenyldimethylamine oxide, dimethylcocamine oxide, dimethyl(hydrogenated beef tallow)amine oxide, bis(hydroxyethyl)cocamine oxide, bis(hydroxyethyl)-(beef tallow)amine oxide bis(hydroxypropyl)stearylamine oxide, bis(hydroxymethyl)behenamine oxide, pentadecyldiethylamine oxide, tridecyldipropylamine oxide, tridecyl-bis(2-hydroxybutyl)amine oxide, heptadecyl-bis(2-hydroxybutyl)amine oxide and tridecyloxypropyl-bis(hydroxyethyl)amine oxide, with lauryldimethylamine oxide, myristyldimethylamine oxide, cetyldimethylamine oxide and stearyldimethylamine oxide being particularly preferred.

Examples of other amphoteric surfactants include imidazoline amphoteric surfactants such as sodium 2-undecyl-N, N,N-(hydroxyethylcarboxymethyl)-2-imidazoline, disodium 2-cocoyl-2-imidazolinium hydroxide-1-carboxyethyloxy; betaine surfactants such as 2 -heptadecyl-N-carboxymethyl-N-hydroxyethylimidazolinium betaine, lauryldimethylaminoacetic acid betaine, alkylbetaines, amidobetaities and sulfobetaines; and salts of amino acids such as N-lauryl β-alanine and N-stearyl β-alanine.

The compounds of component (B) may be used either singly or in any combination thereof, and are preferably incorporated in a range of 0.01–10%, more preferably 0.02–2%, based on the total composition of the cosmetic composition according to the present invention. If no component (B) is added, the stability of the resulting cosmetic composition becomes extremely poor, so that separation or turbidity occurs at high temperatures. If the proportion of the component (B) is lower than 0.01%, it is difficult to achieve a sufficient effect. If the proportion exceeds 10% on the other hand, the resulting gel tends to become too hard.

Suitable water-soluble compounds having at least one hydroxyl group for use as component (C) of the present invention include monoalcohols, dialcohols, polyhydric alcohols, monosaccharides and disaccharides. Preferred compounds include propylene glycol, isoprene glycol (product of Kuraray Co., Ltd.), 1,3-butanediol, dipropylene glycol, glycerol, diglycerol, triglycerol, polyglycerol, trimethylolpropane, erythritol, pentaerythritol, sorbitan, sorbitol, glucose, maltitol, saccharose, trehalose, polyethylene glycol, ethanol and isopropanol, with glycerol, sorbitol, maltitol, ethanol and isopropanol being particularly preferred.

The compounds of component (C) may be used either singly or in any combination thereof, and are preferably incorporated in a range of 10–70%, particularly 30–60% based on the total composition of the cosmetic composition of the present invention.

No particular limitation is imposed on the liquid oil of the component (D) useful in the composition of the present invention. Any conventional liquid oil commonly used in cosmetic compositions is suitable.

The term "liquid oil" as used herein means an oil in the form of liquid or paste at 25° C. Examples include hydrocarbons, higher alcohols, higher fatty acids, higher fatty acid esters of higher alcohols, animal and vegetable oils and fats, cholesterol fatty acid esters, and silicones. Preferred examples include liquid paraffin, polyisobutene, cholesteryl isostearate, glycerol tri-(2-ethylhexanoate), hexadecyl 2-ethylhexanoate, octadecyl myristate, olive oil, and linear or cyclic methylpolysiloxane.

The compounds of component (D) may be used either singly or in any combination thereof, and are preferably incorporated in a range of 1–60%, more preferably 20–40%, based on the total composition of the cosmetic composition of the present invention.

In the present invention, the amount of water to be incorporated as component (E) may be suitably chosen in accordance with the particular end use of the resulting cosmetic composition and properties to be required. Component (E) is preferably incorporated in an amount of 1–87.99%, more preferably 10–40% based on the total composition.

In a further embodiment of the present invention, an additional compound of a sugar derivative and ethylene oxide or propylene oxide may be added as component (F), in addition to the above described components (A) through (E). The addition of component (F) further assists in the prevention of the viscosity increase due to added water and can impart an improved detergency to the composition and give users a more pleasant feeling upon use.

Examples of the addition compound of a sugar derivative include polyoxyalkylene alkyl glycoside ethers, which are obtained by first synthesizing an alkyl glycoside from a starting glucose, and subsequently adding ethylene oxide and/or propylene oxide thereto. Here, it is preferred that the average moles of ethylene oxide and/or propylene oxide added be from 5 to 30 moles in total, and that the alkyl be $C_1$–$C_4$ alkyl, with methyl, ethyl and propyl being preferred and methyl being most preferred.

The compounds of component (F) may be used either singly or in any combination thereof, and are preferably incorporated in a range of 4–50%, more preferably 8–30%, based on the total composition of the present invention. Proportions exceeding 50% give users a disagreeable feeling upon use.

Each of the cosmetic compositions according to the present invention can be prepared by mixing the above-described components using conventional blending methods to form a gel or liquid state. Suitable blending methods can be readily determined in accordance with blending tests for the individual components, which are commonly conducted by those skilled in the art. A basic consideration in the determination of the blending method is to choose the kind and amount of the water-soluble compound and blending ratio, to provide the maximum association of surfactant molecules upon the preparation of the composition according to the present invention. The composition is generally combined by mixing the individual components at a temperature higher than their melting points to melt them and cooling the melt to about room temperature with stirring. In some cases, the thus-obtained cosmetic composition according to the present invention may show optical anisotropy in a range of from about normal temperature to elevated temperatures.

Components which are conventionally used in cosmetic compositions and medicinal compositions may be added to the composition of the present invention. Examples include medicinally-effective ingredients, moisturizing components, antiphlogistic agents, anionic surfactants, disinfectants, antiseptics, ultraviolet absorbents, antioxidants, organic and inorganic powders, colorants and perfume bases, alone or in combination as needed. It is also possible to add solid and semisolid oily substances within limits not impeding the effects of the compositions according to this invention.

The thus-obtained cosmetic compositions of this invention are suitable for use in cleansing, massaging or the like. In particular, they may be preferably used as cleansing preparations for removing makeup from the skin.

The compositions of the present invention have excellent long term storage characteristics, even at high temperatures. The compositions maintain their ability to provide the above described advantages of use for periods exceeding 3 months, even at temperatures of from 25° to 40° C., and even for periods up to 12 months.

Having generally described this invention, a further understanding can be obtained by reference to certain specific examples which are provided herein for purposes of illustration only and are not intended to be limiting unless otherwise specified.

EXAMPLE 1

Cleansing compositions were formulated in accordance with the following procedure to evaluate them in appearance and spreadability. With respect to water resistance, they were evaluated in hardness and spreadability upon use in a bathroom. The results are shown in Tables 1–3. (Preparation procedure)

The various components shown in Tables 1–3 were heated and melted at 80° C. to mix them. The resulting melt mixture was then cooled to near room temperature with stirring, thereby obtaining the respective cleansing compositions. (Evaluation criterion)

Excellent: A
Good: B
Acceptable: C
Unacceptable: D

TABLE 1

| | | Oil-based cosmetic preparation | Invention product | | | | |
|---|---|---|---|---|---|---|---|
| | | | 1 | 2 | 3 | 4 | 5 |
| Comp. (%) | (1) | Polyoxyethylene hardened castor oil (40 E.O., HLB = 13) | 10.0 | 0 | 0 | 0 | 0 |
| | (2) | Polyoxyethylene octyldodecyl ether (20 E.O., HLB = 13) | 0 | 10.0 | 0 | 10.0 | 10.0 |
| | (3) | Polyoxyethylene sorbitan isostearate (20 E.O., HLB = 13) | 0 | 0 | 10.0 | 0 | 0 |
| | (4) | Lauryldimethylamine oxide | 0.6 | 0.6 | 0.6 | 0.6 | 0.6 |
| | (5) | Isotridecyl myristate | 0 | 0 | 0 | 30.0 | 0 |
| | (6) | Glyceryl tri-(2-ethylhexanate) | 30.0 | 30.0 | 30.0 | 0 | 0 |
| | (7) | Neopentylglycol dicaprate | 0 | 0 | 0 | 0 | 30.0 |
| | (8) | Polyisobutene (pentamer) | 0 | 0 | 0 | 0 | 0 |
| | (9) | Polyoxyethylene methylglucoside (10 E.O.) | 18.0 | 18.0 | 18.0 | 18.0 | 18.0 |
| | (10) | Polyoxyethylene methylglucoside (20 E.O.) | 0 | 0 | 0 | 0 | 0 |
| | (11) | Glycerol | 5.0 | 5.0 | 5.0 | 5.0 | 5.0 |

TABLE 1-continued

|  | Oil-based cosmetic preparation |  | Invention product | | | | |
|---|---|---|---|---|---|---|---|
|  |  |  | 1 | 2 | 3 | 4 | 5 |
|  | (12) | Sorbitol | 27.0 | 27.0 | 27.0 | 27.0 | 27.0 |
|  | (13) | Water | 10.0 | 10.0 | 10.0 | 10.0 | 10.0 |
| Appearance (20° C.) | | | Transparent liquid | Transparent liquid | Transparent liquid | Transparent liquid | Transparent liquid |
| Spreadability | | | A | A | A | A | A |
| Water resistance | | Hardness (20° C.) | A | A | A | A | A |
|  | | Spreadability | A | A | A | A | A |

TABLE 2

|  |  | Oil-based cosmetic preparation | Invention product | | |
|---|---|---|---|---|---|
|  |  |  | 6 | 7 | 8 |
| Comp. (%) | (1) | Polyoxyethylene hardened castor oil (40 E.O., HLB = 13) | 0 | 0 | 0 |
|  | (2) | Polyoxyethylene octyldodecyl ether (20 E.O., HLB = 13) | 10.0 | 10.0 | 15.0 |
|  | (3) | Polyoxyethylene sorbitan isostearate (20 E.O., HLB = 13) | 0 | 0 | 0 |
|  | (4) | Lauryldimethylamine oxide | 0.6 | 0.6 | 0.6 |
|  | (5) | Isotridecyl myristate | 0 | 0 | 0 |
|  | (6) | Glyceryl tri-(2-ethylhexanate) | 0 | 30.0 | 30.0 |
|  | (7) | Neopentylglycol dicaprate | 0 | 0 | 0 |
|  | (8) | Polyisobutene (pentamer | 30.0 | 0 | 0 |
|  | (9) | Polyoxyethylene methylglucoside (10 E.O.) | 18.0 | 10.0 | 16.0 |
|  | (10) | Polyoxyethylene methylglucoside (20 E.O.) | 0 | 8.0 | 0 |
|  | (11) | Glycerol | 5.0 | 5.0 | 4.0 |
|  | (12) | Sorbitol | 27.0 | 27.0 | 25.0 |
|  | (13) | Water | 10.0 | 10.0 | 10.0 |
| Appearance (20° C.) | | | Transparent liquid | Transparent liquid | Transparent liquid |
| Spreadability | | | A | A | A |
| Water resistance | | Hardness (20° C.) | A | A | A |
|  | | Spreadability | A | A | A |

TABLE 3

|  |  | Oil-based cosmetic preparation | Comparative product | | |
|---|---|---|---|---|---|
|  |  |  | 1 | 2 | 3*1 |
| Comp. (%) | (1) | Polyoxyethylene hardened castor oil (40 E.O., HLB = 13) | 0 | 0 | 0 |
|  | (2) | Polyoxyethylene octyldodecyl ether (20 E.O., HLB = 13) | 10.0 | 10.0 | 10.0 |
|  | (3) | Polyoxyethylene sorbitan isostearate (20 E.O., HLB = 13) | 0 | 0 | 0 |
|  | (4) | Lauryldimethylamine oxide | 0 | 0 | 0 |
|  | (5) | Isotridecyl myristate | 0 | 0 | 0 |
|  | (6) | Glyceryl tri-(2-ethylhexanate) | 5.0 | 60.0 | 30.0 |
|  | (7) | Neopentylglycol dicaprate | 0 | 0 | 0 |
|  | (8) | Polyisobutene (pentamer | 0 | 0 | 0 |
|  | (9) | Polyoxyethylene methylglucoside (10 E.O.) | 22.5 | 10.0 | 0 |
|  | (10) | Polyoxyethylene methylglucoside (20 E.O.) | 0 | 0 | 0 |
|  | (11) | Glycerol | 7.5 | 2.5 | 10.0 |
|  | (12) | Sorbitol | 40.0 | 12.5 | 40.0 |
|  | (13) | Water | 15.0 | 5.0 | 10.0 |
| Appearance (20° C.) | | | Transparent gel | Transparent gel | Separated |

TABLE 3-continued

| Oil-based cosmetic preparation | | Comparative product | | |
|---|---|---|---|---|
| | | 1 | 2 | 3*[1] |
| Spreadability | | C | B | |
| Water resistance | Hardness (20° C.) | C | C | |
| | Spreadability | C | C | |

*[1]: The properties of Comparative Product 3 could not be determined due to its separation.

As shown in Tables 1–3, the products according to the present invention are in the form of a transparent liquid or gel, spread well and have excellent water resistance. All of the products of the present invention had good massaging ability, were not sticky to the touch, gave users a refreshed feeling after use and a pleasant feeling upon use, and were also excellent in detergency and rinsability.

EXAMPLE 2: CLEANSING COSMETIC PREPARATION

A cleansing cosmetic preparation was formulated by mixing all components of the following composition under heat to melt them, and cooling the resulting melt.

| (Composition) | (%) |
|---|---|
| Polyoxyethylene octyldodecyl ether (20 E.O., HLB = 13) | 12.5 |
| Lauryldimethylamine oxide | 0.3 |
| Polyoxyethylene methylglucoside (10 E.O.) | 15.0 |
| Glycerol tri-(2-ethylhexanoate) | 12.5 |
| Polyisobutene (pentamer) | 12.5 |
| Sorbitol | 33.0 |
| Methyl paraben | 0.1 |
| Butyl paraben | 0.1 |
| Perfume base | 0.1 |
| Purified water | Balance |

Since this cleansing cosmetic preparation was in a liquid state, even dirt in minute parts of the skin could be dispersed or dissolved therein. The composition was easy to use because it could be fully rinsed out with water alone after completion of cleansing. It was also excellent in cleansing power.

EXAMPLE 3: CLEANSING COSMETIC PREPARATION

A cleansing cosmetic preparation was formulated by mixing all components of the following composition under heat to melt them, and cooling the resulting melt.

| (Composition) | (%) |
|---|---|
| Polyoxyethylene octyldodecyl ether (20 E.O., HLB = 13) | 8.0 |
| Polyoxyethylene hardened castor oil (60 E.O., HLB = 14) | 5.0 |
| Polyoxyethylene hardened castor oil (10 E.O., HLB = 6) | 1.0 |
| Lauryldimethylamine oxide | 0.16 |
| Polyoxyethylene methylglucoside (10 E.O.) | 15.0 |
| Glycerol tri-(2-ethylhexanoate) | 12.5 |
| Liquid paraffin | 12.5 |
| Sorbitol | 28.0 |
| Glycerol | 5.0 |
| Methyl paraben | 0.1 |

| (Composition) -continued | (%) |
|---|---|
| Butyl paraben | 0.1 |
| Perfume base | 0.1 |
| Ethanol | 1.0 |
| Purified water | Balance |

Since this cleansing cosmetic preparation was a gel, even dirt in minute parts of the skin could be dispersed or dissolved therein. As in Example 2, this composition was easy to use, since it could be fully rinsed out with water alone after completion of cleansing. It was also excellent in cleansing power.

EXAMPLE 4: MASSAGING CREAM

A massaging cream was formulated by mixing all components of the following composition under heat to melt them, and cooling the resulting melt.

| (Composition) | (%) |
|---|---|
| Polyoxyethylene octyldodecyl ether (20 E.O., HLB = 13) | 12.5 |
| Lauryldimethylamine oxide | 0.2 |
| Polyoxyethylene methylglucoside (10 E.O.) | 15.0 |
| Neopentylglycol dicaprate | 15.0 |
| Glycerol tri-(2-ethylhexanoate) | 7.5 |
| Liquid paraffin | 7.5 |
| Sorbitol | 28.0 |
| Glycerol | 5.0 |
| Methyl paraben | 0.1 |
| Ethyl paraben | 0.1 |
| Butyl paraben | 0.1 |
| Perfume base | 0.1 |
| Ethanol | 1.0 |
| dl-α-Tocopheryl acetate | 0.1 |
| Purified water | Balance |

Once again, this massaging cream was a gel. Thus, even dirt in minute parts of the skin could be dispersed or dissolved therein. It was easy to use, since it could be fully rinsed out with water alone after completion of massaging. It was also excellent in cleansing power.

EXAMPLE 5: CLEANSING COSMETIC PREPARATION

A cleansing cosmetic preparation was formulated by mixing all components of the following composition under heat to melt them, and cooling the resulting melt.

| (Composition) | (%) |
| --- | --- |
| Polyoxyethylene octyldodecyl ether (20 E.O., HLB = 13) | 10.0 |
| Polyoxyethylene hardened castor oil (60 E.O., HLB = 14) | 3.0 |
| Polyoxyethylene hardened castor oil (10 E.O., HLB = 6) | 1.0 |
| Lauryldimethylamine oxide | 0.16 |
| Glycerol tri-(2-ethylhexanoate) | 12.5 |
| Liquid paraffin | 12.5 |
| Sorbitol | 33.0 |
| Glycerol | 15.0 |

What is claimed as new and desired to be secured by Letters Patent of the United States is:

1. A cosmetic composition, comprising the following components (A) through (E):
   (A) 1–30 wt. % of a hydrophilic nonionic surfactant selected from the group consisting of polyoxyethylene hardened castor oil, polyoxyethylene octyldodecyl ether and polyoxyethylene sorbitan isostearate;
   (B) 0.01–10 wt. % of lauryldimethylamine oxide as amphoteric surfactant;
   (C) 10–70 wt. % of a water-soluble compound containing at least one hydroxyl group selected from the group consisting of glycerol and sorbitol;
   (D) 20–40 wt. % of a liquid oil selected from the group consisting of polyisobutene, glyceryl tri-(2-ethylhexanoate), isotridecyl myristate, and neopentylglycol dicaprate; and
   (E) 1–40 wt. % of water.

2. A cosmetic composition, comprising the following components (A) through (F):
   (A) 1–30 wt. % of a hydrophilic nonionic surfactant selected from the group consisting of polyoxyethylene hardened castor oil, polyoxyethylene octyldodecyl ether and polyoxyethylene sorbitan isostearate;
   (B) 0.01–10 wt. % of lauryldimethylamine oxide as amphoteric surfactant;
   (C) 10–70 wt. % of a water-soluble compound containing at least one hydroxyl group selected from the group consisting of glycerol and sorbitol;
   (D) 20–40 wt. % of a liquid oil selected from the group consisting of polyisobutene, glyceryl tri-(2-ethylhexanoate), isotridecyl myristate, and neopentylglycol dicaprate;
   (E) 1–40 wt. % of water; and
   (F) 4–50 wt. % of a compound selected from the group consisting of polyoxyethylene methyl glucoside(10 E.O.) and polyoxyethylene methylglucoside(20 E.O.).

* * * * *